United States Patent [19]

Diaz et al.

[11] Patent Number: 4,826,480
[45] Date of Patent: May 2, 1989

[54] OMENTUM DIFFUSION CATHETER

[75] Inventors: Raul Diaz, Laguna Niguel; Mark W. Davis, Thousand Oaks, both of Calif.

[73] Assignee: Pacesetter Infusion, Ltd., Sylmar, Calif.

[21] Appl. No.: 43,796

[22] Filed: Apr. 29, 1987

[51] Int. Cl.$^4$ .................... A61M 5/00; A61M 25/00
[52] U.S. Cl. ........................ 604/49; 604/93; 604/175; 604/275; 604/280
[58] Field of Search ............ 604/19, 48, 49, 93, 604/175, 240, 266, 280, 283, 275, 264; 285/260, 294, 297, 304

[56] References Cited

U.S. PATENT DOCUMENTS

| | | | |
|---|---|---|---|
| 2,785,910 | 3/1957 | Munger | 285/297 |
| 2,985,469 | 5/1961 | Bowman, Jr. | 285/260 |
| 3,022,209 | 2/1962 | Campbell | 285/260 |
| 3,904,808 | 9/1975 | Kriechbaum | 285/294 |
| 3,920,787 | 11/1975 | McDowell et al. | 285/297 |
| 4,160,454 | 7/1979 | Foux | 128/348 |
| 4,278,092 | 7/1981 | Borsanyi et al. | 128/348 |
| 4,368,737 | 1/1983 | Ash | 604/175 |
| 4,398,910 | 8/1983 | Blake et al. | 604/266 |
| 4,416,657 | 11/1983 | Berglund | 604/9 |
| 4,430,080 | 2/1984 | Pasquini et al. | 604/240 |
| 4,465,481 | 8/1984 | Blake | 604/280 |
| 4,488,877 | 12/1984 | Klein et al. | 604/175 |
| 4,490,137 | 12/1984 | Moukheibir | 604/28 |
| 4,523,920 | 6/1985 | Russo | 604/280 |
| 4,536,179 | 8/1985 | Anderson et al. | 604/266 |
| 4,557,724 | 10/1985 | Gregonis et al. | 604/49 |
| 4,559,033 | 12/1985 | Stephen et al. | 604/49 |
| 4,559,951 | 12/1985 | Dahl et al. | 128/642 |
| 4,581,390 | 4/1986 | Flynn | 604/280 |

FOREIGN PATENT DOCUMENTS

| | | | |
|---|---|---|---|
| 0151519 | 8/1985 | European Pat. Off. | 604/283 |
| 8500526 | 2/1985 | World Int. Prop. O. | 604/266 |

Primary Examiner—Dalton L. Truluck
Attorney, Agent, or Firm—Leslie S. Miller

[57] ABSTRACT

An implantable catheter for use in delivering insulin or other therapeutic fluids is disclosed which uses a novel terminator design to prevent the growth of fibrotic tissue from obstruction the catheter. The catheter takes advantage of fibrotic encapsulation by utilizing a depression in the surface of the terminator which will effectively keep fibrotic tissue spaced sufficiently away therefrom to allow fluid to be infused. In addition to being capable of long term implant, the catheter is implantable in the omentum, enabling the body's natural absorption of insulin to be successfully mimicked.

23 Claims, 2 Drawing Sheets

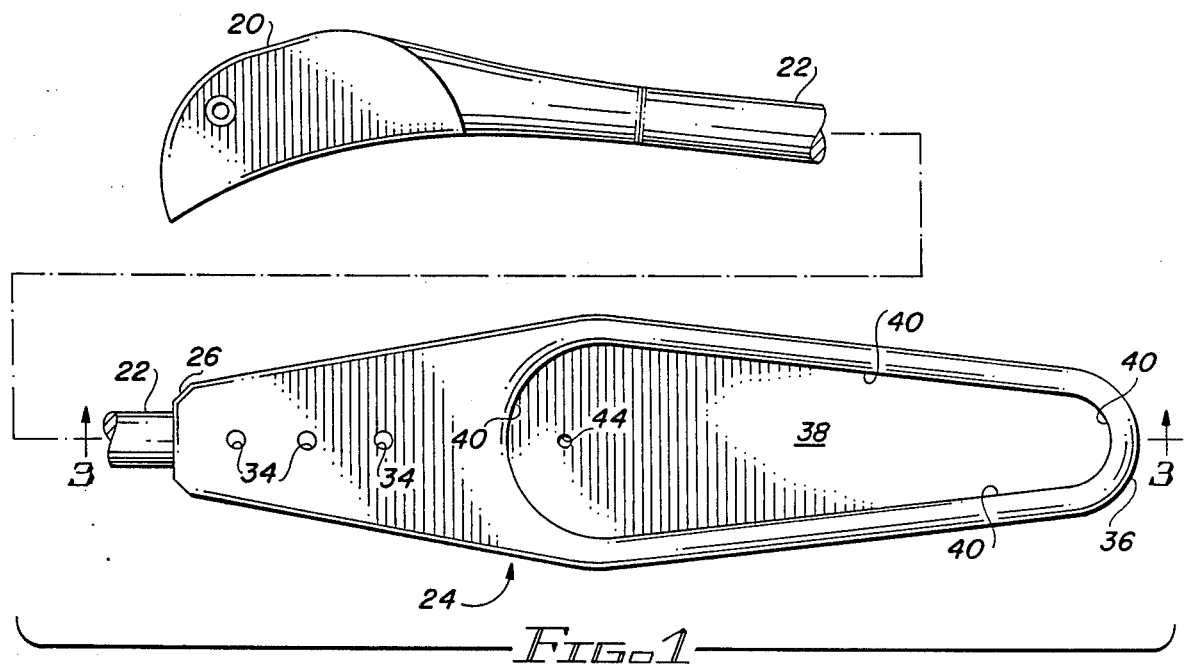
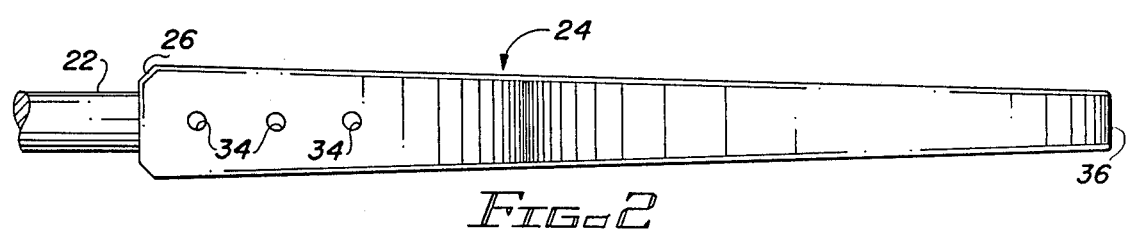
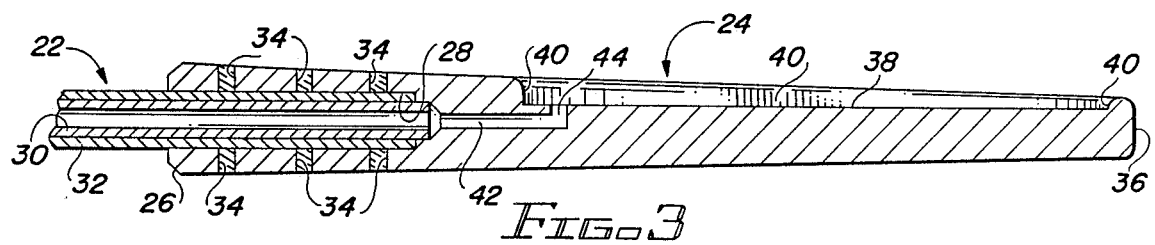
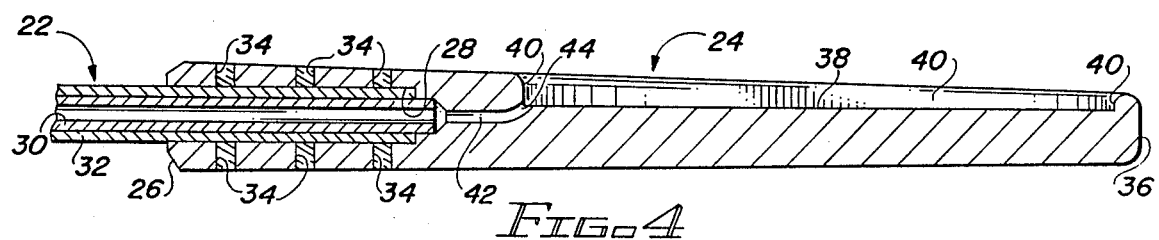
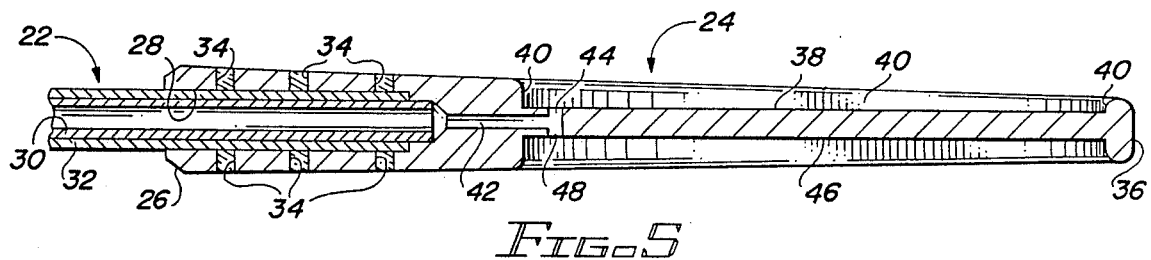

OMENTUM DIFFUSION CATHETER

BACKGROUND OF THE INVENTION

Field of the Invention

The present invention relates generally to an implantable catheter for use in the infusion of a therapeutic fluid into a living patient over a substantial period of time, and more particularly to an implantable catheter which both exhibits substantial resistance to flow diminution or elimination due to the growth of fibrotic tissue around the catheter and exhibits enhanced absorption kinetics.

Metabolism of glucose in the body is a particularly important chemical reaction which allows the utilization of the energy contained in food. The physiological system of the body has a sophisticated regulatory system which, when operating properly, maintains the level of blood glucose at an optimum level, thereby assuring the availability of adequate amounts of glucose when needed by the body.

This glucose regulatory system utilizes insulin to regulate blood glucose in two ways. First, the rate of glucose transport through the cell membrane of many body cell types is increased by insulin. In the absence of insulin, the rate of glucose transport through such cells is dramatically reduced to less than one-fourth the normal rate of glucose transport. However excessively high insulin levels can greatly increase the rate of glucose transport to five times the normal rate. It is thereby apparent that insulin level has at least the capacity to adjust the rate of glucose absorption in the body by a factor of twenty.

Secondly, insulin acts as a regulatory hormone which is supplied to the liver. The secretion of insulin by the pancreas is stimulated by digestion and the accompanying higher glucose levels in the body, resulting in an increase in the amount of insulin secreted into the portal vein. While approximately half of the insulin secreted into the portal vein is distributed throughout the body by the cardiovascular system, the rest of the insulin is immediately absorbed by the liver. In response to the surge of insulin, the liver produces large quantities of glucokinase, an enzyme enabling conversion of glucose into glycogen, which may be stored by the body. Much of the excess glucose entering the cardiovascular system as a result of digestion is thereby quickly removed to maintain relatively normal levels of glucose concentration in the blood.

When the level of glucose concentration in the blood later begins to drop below normal, the level of insulin secretion by the pancreas is reduced, and production of the hormone glucagon is begun. Glucagon enables the conversion of glycogen in the liver back into glucose by activating liver phosphorylase, an enzyme, and the result is the release of glucose into the cardiovascular system for distribution throughout the body. Once again, the body acts to maintain the concentration of glucose in the blood at a normal level.

The system which maintains a normal level of blood glucose is finely balanced, and the relationship between the pancreas and the liver can be easily upset. The most common problem is the situation when the pancreas no longer secretes adequate levels of insulin, a condition known as "diabetes mellitus." In some instances, the pancreas may completely cease the production of insulin.

In any event, the diminution or reduction in insulin production results in a rise in the concentration of glucose in the blood, which causes the osmotic pressure in extracellular fluids to rise above normal pressure. The result of this increase in osmotic pressure is typically significant cellular dehydration. The increase in the blood glucose concentration also affects the kidneys, thereby causing them to act to remove excess glucose from the blood, in which process fluids are further removed from the body.

The diminution of insulin production is also accompanied by a substantial reduction in the transportation of glucose into most tissues of the body. In addition, an insulin shortage also prevents glucose from being stored in the liver as glycogen, thereby resulting in a lack of available glucose in the times of glucose need. In conditions in which there is an absence of sufficient levels of glucose, body cell metabolism becomes fat based instead of carbohydrate based Heavy dependence on fat metabolism due to insufficient blood glucose concentration results in a substantial rise in the concentration of acetoacetic acid and other keto acids to as much as thirty times normal levels, thereby causing a significant reduction in the pH of blood below its normal pH level of 7.4.

When the kidneys attempt to alleviate the concentration of the various keto acids in the blood, substantial amounts of sodium are also removed, thereby further lowering the blood pH. Should the blood pH fall below 7.0, a coma state will typically be experienced, with the results frequently being fatal.

Diabetic treatment has centered on restoring proper carbohydrate metabolism by the administration of insulin. For years insulin has been administered by multiple daily injections into the peripheral circulation, either by intramuscular or subcutaneous injection. More recently, insulin infusion pumps have been used to deliver insulin from a small, portable insulin infusion pump to a subcutaneous injection location on a more or less continuous basis. Both of these techniques have certain disadvantages, particularly the multiple daily injection technique.

Peripheral insulin administration results in only about ten percent of the insulin administered reaching the liver, as compared to the fifty percent or so in normal individuals. Therefore, rather than hepatic glucose production being lowered first, blood glucose level is reduced due to the presence of higher than normal levels of insulin in the peripheral circulation by an increased utilization of glucose by body tissues. It is more difficult to maintain a normal level of blood glucose by using insulin injection, since, unlike the natural feedback system of the body, hepatic glucose production is not substantially decreased by insulin which is injected peripherally.

It is therefore apparent that it would be desirable to administer insulin to a patient in a manner whereby a greater percentage of the insulin reaches the liver than in peripheral administration of insulin A catheter which would deliver insulin internally rather than peripherally would accomplish this objective, but since it would be internally implanted it would have to be capable of continuing to function effectively over an extended period of time.

The problem with implantable catheters is that they rapidly tend to become overgrown with fibrotic tissue which will close off the catheter in short order. This is particularly true in those cases where only a small flow of medication is being delivered through the catheter. Several types of catheters have been used, with the most common being a simple tube having an aperture therethrough. At the end of the tube, the aperture allows medication to exit the tube and enter the body. It will be appreciated that such an arrangement is susceptible to being covered with fibrotic tissue relatively rapidly, since the fibrotic tissue will grow around the end of the tube.

Variations include the addition of a disk which is mounted at the end of the catheter with the tube leading orthogonally to the disk with medication exiting the aperture of the tube at the center of the disk. While this design is somewhat less susceptible to clogging by the rapid growth of fibrotic tissue, in time the entire disk will be covered and the opening will be closed by the fibrotic tissue. The other approach that has been used is to make the opening of a small diameter to cause the fluid to exit the catheter with a relatively high velocity.

It will be appreciated that these approaches leave something to be desired in an implantable catheter Since the implantation of a catheter generally involves major surgery, it is desirable that an implantable catheter be capable of operating over an extended period of time without requiring repair or replacement. Since catheters known in the art do not meet this need, the use of implantable catheters has been minimized to prevent the adverse effect of requiring frequent catheter repair or replacement

SUMMARY OF THE INVENTION

The disadvantages and imitations of the background art discussed above are overcome by the present invention. With this invention, an implantable catheter having a novel delivery end configuration is implanted in the tissue of the omentum. The distal or delivery end is placed into a fold in the omentum tissue, which is then sutured around the delivery end of the catheter.

The present invention utilizes a novel configuration for the distal or delivery end of the catheter which greatly inhibits the ability of fibrotic tissue to choke off fluid delivered through the catheter. The configuration may be loosely called a "spoon," since it superficially resembles a spoon, but will be referred to herein as a catheter terminator. The terminator includes an area having well defined walls around the area, thereby creating a recessed area. Insulin (or another therapeutic fluid) is supplied through the catheter to the terminator, where it is supplied to a location on said recessed area relatively near one or more of the walls through a passageway in the terminator which leads to an aperture in the recessed area.

The location of the terminator of the catheter in the omentum tissue is an ideal location The insulin will be absorbed effectively in a manner mimicking to the greatest extent possible the body's utilization of insulin The terminator of the catheter will be held in a secure location, with predictable absorption of the insulin. In addition, fibrotic tissue growth may happen at a somewhat reduced pace from other locations in the body.

In a first embodiment, the distal or delivery end is a plastic terminator which includes at least one recessed surface or depression therein A segment of tubing connects the proximal end of the catheter, usually a pump connector, to the terminator of the catheter. The tubing may be connected to the terminator in a variety of ways, such as by insertion of the tubing into a cylindrical recess in the terminator, or by extending the tubing over one or more tapered frictional ridges on the terminator.

A passageway in the terminator communicating with the tubing provides a supply of insulin from the tubing to the interior of the terminator The passageway communicates with the recessed surface through an aperture located near the edge of the recessed surface, and therefore near a wall defining the edge of the recessed surface.

The aperture could also be located right at the edge between the recessed surface and the wall. Also, the terminator may have a recessed surface in the opposite side of the terminator from the first recessed surface, with a second aperture leading from the passageway to the second recessed surface.

In a second embodiment, a plastic terminator is shaped more like the blade of a shovel than a spoon. The recessed area is formed by a longitudinal segment of a cylinder, typically of approximately 120-220 degrees, with one end closed. A passageway delivers insulin to an aperture located in the closed end, near to the cylindrical segment. The same type of connecting means described above may be used to connect the terminator to the tubing.

While fibrotic tissue will grow around the catheter, occlusion of the aperture is prevented in both embodiments by the fact that the recessed surface is spaced away from the place where fibrotic tissue will grow. In the first embodiment, the walls surrounding the recessed surface support the fibrotic tissue away from the recessed surface, particularly the portion of the recessed surface near the walls where the aperture is located. In the second embodiment, the cylindrical segment performs the same function, supporting fibrotic tissue away from the area inside the cylindrical segment and the aperture.

The effect of supporting the fibrotic tissue away from the recessed surface is to provide a pool area for the insulin as it exits the terminator through the aperture, thereby also aiding in absorption of the insulin. It will be realized that the design of the catheter of the present invention provides a more viable alternative for long term use than previously available catheters. It is capable of long term use without succumbing to catheter blockage due to the growth of fibrotic tissue around the terminator. It is of inexpensive construction, and affords substantially no relative disadvantages over other catheter designs. Its location in the omentum successfully mimics the body's absorption of insulin. It may therefore be perceived that the present invention affords substantial advantage over the art and is a highly desirable approach.

DESCRIPTION OF THE DRAWINGS

These and other advantages of the present invention are best understood with reference to the drawings, in which:

FIG. 1 is a top view of a catheter constructed according to the teaching of the present invention;

FIG. 2 is a side view of the terminator of the catheter shown in FIG. 1;

FIG. 3 is a sectional view of the catheter shown in FIGS. 1-2;

FIG. 4 is a sectional view of a first alternate construction to the catheter shown in FIGS. 1-3;

FIG. 5 is a sectional view of a second alternate construction to the catheter shown in FIGS. 1-3;

DETAILED DESCRIPTION OF THE PREFERRED EMBODIMENT

Figure 6:
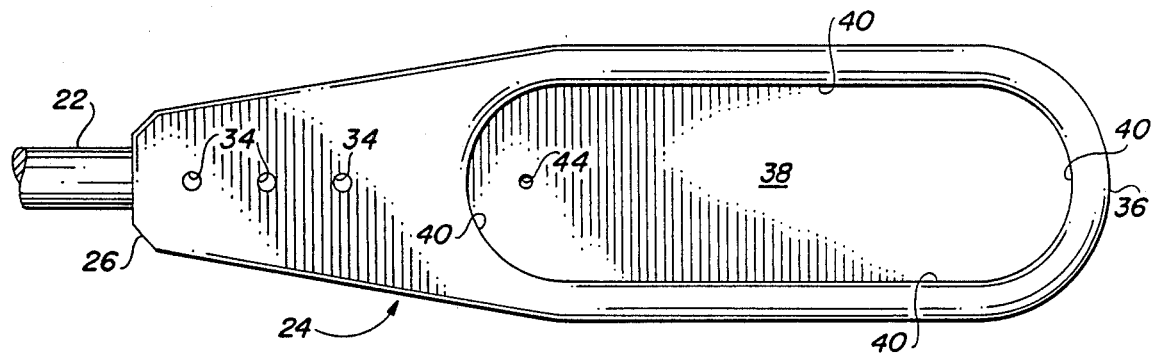
FIG. 6 is a top view of a catheter which is the first alternate embodiment of the present invention.
Figure 7:
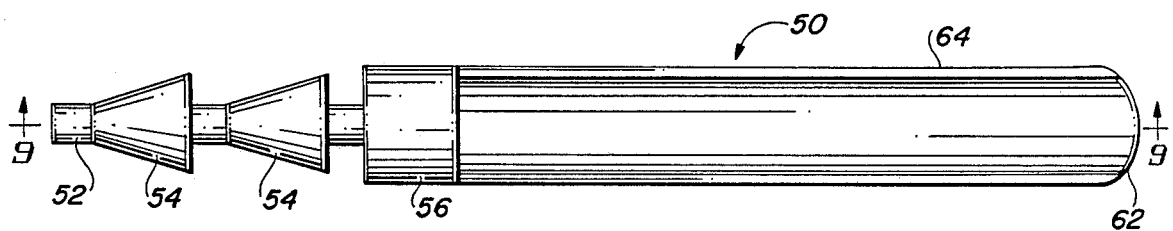
FIG. 7 is a top view of a terminator for a catheter which is the second alternate embodiment of the present invention.
Figure 8:
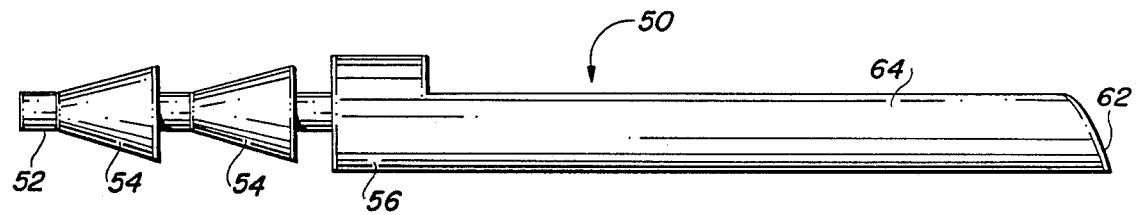
FIG. 8 is a side view of the terminator of the catheter shown in FIG. 7.
Figure 9:
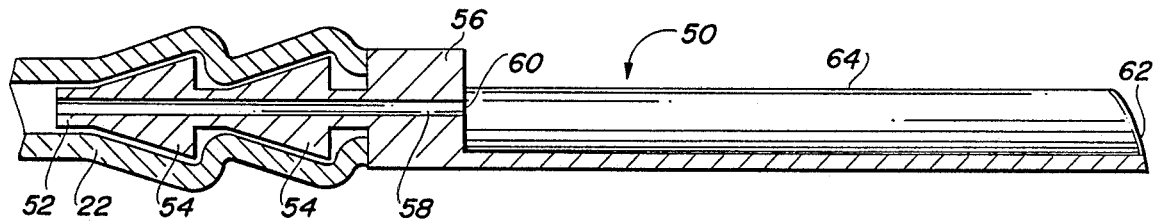
FIG. 9 is a sectional view of the terminator of the catheter shown in FIGS. 7-8.
Figure 10:
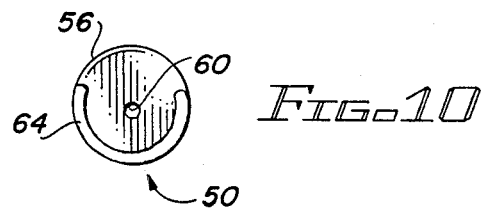
FIG. 10 is an end view of the terminator of the catheter shown in FIGS. 7-9, showing the curved configuration of the terminator.

The first embodiment in its preferred construction is illustrated in FIGS. 1-3. A pump connector 20 of conventional construction for the infusion pump (not shown) is to be used as the proximal end of the catheter, and is connected to a length of tubing 22. The other end of the tubing 22 is connected to a catheter terminator 24 at the proximal end 26 of the catheter terminator 24.

The catheter terminator 24 has a longitudinally extending cylindrical recess 28 in the proximal end 26 of the catheter terminator 24 for receiving the end of the tubing 22 which is not connected to the pump connector 20. The tubing 22 may be made of any medical grade material such as silastic, but is preferably constructed using multiwall tubing having as an annular inner layer polyethylene and as an annular outer layer silicone rubber or another suitable implantable medical grade material In order to utilize the catheter of the present invention with insulin, a coextruded or two layer tubing is necessary. Multiwall tubing is generally manufactured by extruding the inner or innermost tubing first, and successively extruding an outer annular layer around the previously extruded inner layer.

The tubing 22 may be bonded to the cylindrical recess 28 to form a strong, durable seal with excellent shelf life characteristics in an economical, highly repeatable operation. Alternatively, the catheter terminator 24 may be made of polyethylene, and have a number of small apertures 34 on the top, bottom, and sides of the proximal end 26 of the catheter terminator 24, which small apertures 34 lead into the cylindrical recess 28. In this case, as illustrated in the figures, the tubing 22 may be inserted into the cylindrical recess 28, and medical adhesive adhering only to the tubing 22 may be applied through the small apertures 34. In this case, the mechanical bond between the cured adhesive in the small apertures 34 and the outer layer 32 of the tubing 22 provides the force retaining the tubing 22 in the cylindrical recess 28.

The configuration of the catheter terminator 24 is specifically designed to facilitate long term implantation without catheter blockage due to the growth of fibrotic tissue. Since it is recognized that some degree of encapsulation of the catheter terminator 24 by fibrotic tissue is inevitable, the design of the catheter terminator 24 takes advantage of the encapsulation by choosing the form and configuration of the encapsulation. It will be noted that the overall configuration of the catheter terminator 24 is accomplished to eliminate sharp edges, thereby minimizing encapsulation due to irritation or rejection.

Specifically, the distal end 36 of the catheter terminator 24 is rounded, and the thickness of the catheter terminator 24 is tapered from the proximal end 26 to the distal end 36, as best shown in FIG. 2. The width of the catheter terminator 24 is of diminishing taper on both the proximal end 26 and the distal end 36 as shown in FIG. 1, with the maximum width being approximately one-third of the way from the proximal end 26 toward the distal end 36. The diminishing taper on the proximal end 26 of the catheter terminator 24 is necessary to facilitate removal of the catheter, if it should become necessary to do so.

On the top surface of the catheter terminator 24 is a depression 38 extending from the widest part of the catheter terminator 24 to the distal end 36 of the catheter terminator 24. The depression 38 is close to the sides of the catheter terminator 24, and the wall 40 on the edges of the depression 38 rises sharply from the depression 38. It will at once be appreciated by those skilled in the art that as the catheter terminator 24 becomes encapsulated in fibrotic tissue, the fibrotic tissue will not as easily conform to the depression 38, particularly to those portions of the depression 38 near the wall 40.

Within the catheter terminator 24 is a passageway 42 leading from the interior of the tubing 22 to an aperture 44 in the depression 38. The passageway 42 may have a right angle bend in it, as shown in FIG. 3, or it may have a gentler bend or a curve in it as shown in FIG. 4. The important consideration is that the aperture 44 in the depression 38 be located relatively near the wall 40, as opposed to being located centrally in the depression 38. The aperture 44 in the depression 38 may be located a short distance away from the wall 40 as shown in FIG. 3, or it may be located in the edge between the depression 38 and the wall 40, as shown in FIG. 4. It is also within the scope of the invention to locate the aperture 44 on the wall 44 rather than in the depression 38.

A variation of this construction is shown in FIG. 5, which is like the catheter terminator 24 shown in FIGS. 1-3, with the exception that a second depression 46 is added to the bottom of the catheter terminator 24. In addition, the passageway 42 also leads to a second aperture 48 in the second depression 46.

A second variation is shown in FIG. 6, with the catheter terminator 24 not having a diminishing taper on the distal end 36.

The typical size of the terminator 24 may be, for example, approximately one and one-half inches long, seven-sixteenths of an inch wide, and from one-tenth to three twentieths of an inch in thickness, although it will be recognized by those skilled in the art that the size may vary significantly without departing from the spirit of the invention.

In FIGS. 7-10, a second embodiment of the catheter of the present invention is shown. A catheter terminator 50 has at the proximal end 52 two tapered frictional ridges 54 used to sealingly retain the tubing 22 thereon. Inside the two tapered frictional ridges 54 to a cylindrical portion 56 of the catheter terminator 50 is a passageway 58 leading to an aperture 60 in the end of the cylindrical portion 56 of the catheter terminator 50 facing the distal end 62 of the catheter terminator 50.

Extending from the end of the cylindrical portion 56 of the catheter terminator 50 facing the distal end 62 of the catheter terminator 50 is a curved surface 64 which is a longitudinal segment of a cylinder the same diameter and colinear with the cylindrical portion 56 of the catheter terminator 50. The curved surface 64 is typically from a 120 to 220 degrees segment of a cylinder, and may also be U-shaped rather than arcuate in cross-section.

The aperture 60 is located near to the inner surface of the curved surface 64; alternatively, if the curved surface 64 is of sufficient curvature, the aperture 60 may be located centrally in the cylindrical portion 56 of the catheter terminator 50. It will again be appreciated by those skilled in the art that the catheter terminator 50 will also be highly resistant to occlusion caused by the growth of fibrotic tissue The typical size of the terminator 50 may be, for example, approximately one and one-fourth inches long and one-eighth of an inch in diameter, although again it will be recognized by those skilled in the art that the size may vary significantly without departing from the spirit of the invention. It will also be recognized that the diameter is critical, since the inner curvature must be small enough to inhibit fibrotic tissue from conforming thereto.

The catheters using the terminators 24 or 50 may be implanted in the tissue of the omentum (not shown), with a fold of omentum tissue being sutured around the terminators 24 or 50. The location of the terminator of the catheter in the omentum tissue is an ideal location, since the insulin will be absorbed effectively in a manner mimicking to the greatest extent possible the body's utilization of insulin and the terminator 24 or 50 will be held in a secure location The effect of supporting the fibrotic tissue away from the depression 38 (and 46) or the inside of the curved surface 64 is to provide a pool are for the insulin as it exits the terminator 24 or 50 through the aperture 44 (and 48) or 60, thereby also aiding in absorption of the insulin. The design of the catheter of the present invention provides a more viable alternative for long term use than previously available catheters, since it is capable of long term use without succumbing to catheter blockage due to the growth of fibrotic tissue. It is of inexpensive construction, and affords substantially no relative disadvantages over other catheter designs while attaining the advantages enumerated herein. The present invention therefore affords a substantial number of advantages over the art and is a highly desirable device.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. An implantable catheter for placement in the omentum tissues, comprising:
    a length of tubing;
    means for connecting said infusion pump to one end of said length of tubing to supply fluid from said infusion pump to said length of tubing;
    a catheter terminator having a recessed area thereon, said catheter terminator having a diminishing taper at the proximal end thereof, said catheter terminator maintaining fibrotic tissue growth away from said recessed area, said catheter terminator for implantation in the omentum tissue;
    a passageway within said catheter terminator, the other end of said length of tubing being attached to said catheter terminator to supply fluid from said tubing to said passageway, said passageway leading to an aperture located near to said recessed area;
    a cylindrical recess in the proximal end of said catheter terminator for receiving said other end of said length of tubing said cylindrical recess communicating with said passageway at the end of said cylindrical passageway closest the distal end of said catheter terminator;
    a plurality of small apertures on the top bottom, and sides of said proximal end of said catheter terminator leading into said cylindrical recess; and
    medical adhesive installed in said small apertures after said other end of said length of tubing is installed into said cylindrical recess to retain said other end of said length of tubing is said cylindrical recess.

2. An implantable catheter as defined in claim 1, wherein said tubing is made of medical grade silastic.

3. An implantable catheter as defined in claim 1, wherein said tubing is of multiwall construction and has an annular inner layer of polyethylene and an annular outer layer of silicone rubber.

4. An implantable catheter as defined in claim 1, wherein said connecting means comprises:
    a pump connector for connection to an infusion pump, said pump connector in fluid communication with a fluid output of said pump.

5. An implantable terminator catheter as defined in claim 1, wherein said catheter terminator is made of polyethylene.

6. An implantable catheter as defined in claim 1, wherein said catheter terminator has a first recessed area on one side thereof and a second recessed area on the other side thereof, said passageway leading to a first aperture located near to said first recessed area and a second aperture located near to said second recessed area.

7. An implantable catheter as defined in claim 1, wherein said recessed area is defined at least in part by a wall rising from the edge of said recessed area.

8. An implantable catheter as defined in claim 7, wherein said aperture is located in said recessed area near to said wall.

9. An implantable catheter as defined in claim 7, wherein said aperture is located in said wall near to said recessed area.

10. An implantable catheter as defined in claim 7, wherein said aperture is located at the intersection between said recessed area and said wall.

11. An implantable catheter as defined in claim 7, wherein said wall extends circumferentially around said recessed area.

12. An implantable catheter for placement in the omentum tissues, comprising:
    a pump connector for connection to an infusion pump, said pump connector being in fluid communication with a fluid output of said pump;
    a length of tubing connected at one end thereof to said pump connector, said length of tubing being in fluid communication with said pump connector;
    a catheter terminator having a proximal end and a distal end, said proximal end of said catheter terminator being connected to the other end of said length of tubing, said catheter terminator having a diminishing taper at the proximal end thereof, said catheter terminator having a passageway disposed therein which passageway is in fluid communication with said length of tubing, said catheter terminator also having a recessed area extending from said distal end of said catheter terminator to a point intermediate said proximal and distal ends of said catheter terminator, said recessed area being surrounded by a wall portion of said catheter terminator extending above said recessed area to maintain fibrotic tissue growth away from said recessed area, said passageway terminating in an aperture in said recessed area near the edge of said recessed area; and means for fixedly receiving said other end of said length of tubing, said receiving means being constructed integrally with said catheter terminator.

13. An implantable catheter for supplying fluid from an infusion pump to the omentum tissues, comprising:

a pump connector for removable connection to said infusion pump, said pump connector being in fluid communication with a fluid output of said pump;

a length of hollow tubing connected at one end thereof to said pump connector, said length of tubing being in fluid communication with said pump connector;

a catheter terminator having a proximal end and a distal end, said proximal end of said catheter terminator including means for connection to the other end of said length of tubing, said catheter terminator having a passageway disposed therein which passageway is in fluid communication with said length of tubing, said catheter terminator having a diminishing taper at the proximal end thereof;

a recessed area in said catheter terminator, said recessed area extending from a location near said distal end of said catheter terminator to a point intermediate said proximal and distal ends of said catheter terminator, said recessed area being surrounded on at least three sides by a wall portion which is raised with respect to said recessed area, said passageway terminating in an aperture in said recessed area near the edge of said recessed area, said raised portion of said catheter terminator thereby extending above said recessed area to maintain fibrotic tissue growth away from said recessed area to allow fluid to freely exit said aperture;

a cylindrical recess in the proximal end of said catheter terminator for receiving said other end of said length of tubing, said cylindrical recess communicating with said passageway at the end of said cylindrical passageway closest the distal end of said catheter terminator;

a plurality of small apertures on the top bottom, and sides of said proximal end of said catheter terminator leading into said cylindrical recess; and medical adhesive installed in said small apertures after said other end of said length of tubing is installed into said cylindrical recess to retain said other end of said length of tubing is said cylindrical recess.

14. A method of supplying fluid from an infusion pump to the omental tissue, comprising:

connecting said infusion pump to a length of tubing to supply fluid from said infusion pump to said length of tubing;

providing a catheter terminator having a recessed area thereon, said catheter terminator having a diminishing taper at the proximal end thereof, said catheter terminator maintaining fibrotic tissue growth away from said recessed area, said catheter terminator for implantation in the omentum tissue;

attaching said length of tubing to said catheter terminator to supply fluid from said tubing to a passageway within said catheter terminator; and supplying fluid from said catheter terminator through an aperture leading from said passageway, said aperture being located near to said recessed area.

15. An implantable catheter for placement in the omentum tissues, comprising:

a length of tubing;

means for connecting said infusion pump to one end of said length of tubing to supply fluid from said infusion pump to said length of tubing;

a catheter terminator having a recessed area thereon, said catheter terminator having a diminishing taper at the proximal end thereof, said catheter terminator maintaining fibrotic tissue growth away from said recessed area, said catheter terminator for implantation in the omentum tissue;

a passageway within said catheter terminator, the other end of said length of tubing being attached to said catheter terminator to supply fluid from said tubing to said passageway, said passageway leading to an aperture located near to said recessed area;

means for fixedly receiving said other end of said length of tubing, said receiving means being constructed integrally with said catheter terminator; and a plurality of tapered frictional ridges integrally constructed with said catheter terminator at the proximal end thereof, said tapered frictional ridges allowing said other end of said length of tubing to be slideably installed thereover, and resisting the removal of said other end of said length of tubing from said tapered frictional ridges once installed, said passageway extending centrally through the portion of said catheter terminator containing said tapered frictional ridges.

16. An implantable catheter as defined in claim 15, wherein said tubing is of multiwall construction and has an annular inner layer of polyethylene and an annular outer layer of silicone rubber.

17. An implantable catheter as defined in claim 15, wherein said catheter terminator has a first recessed area on one side thereof and a second recessed area on the other side thereof, said passageway leading to a first aperture located near to said first recessed area and a second aperture located near to said second recessed area.

18. An implantable catheter as defined in claim 15, wherein said recessed area is defined at least in part by a wall rising from the edge of said recessed area.

19. An implantable catheter as defined in claim 18, wherein said aperture is located in said recessed area near to said wall.

20. An implantable catheter as defined in claim 18, wherein said aperture is located in said wall near to said recessed area.

21. An implantable catheter as defined in claim 18, wherein said aperture is located at the intersection between said recessed area and said wall.

22. An implantable catheter as defined in claim 18, wherein said wall extends circumferentially around said recessed area.

23. An implantable catheter for supplying fluid from an infusion pump to the omentum tissues, comprising:

a pump connector for removable connection to said infusion pump, said pump connector being in fluid communication with a fluid output of said pump;

a length of hollow tubing connected at one end thereof to said pump connector, said length of tubing being in fluid communication with said pump connector;

a catheter terminator having a proximal end and a distal end, said proximal end of said catheter terminator including means for connection to the other end of said length of tubing, said catheter terminator having a passageway disposed therein which passageway is in fluid communication with said length of tubing, said catheter terminator having a diminishing taper at the proximal end thereof;

a recessed area in said catheter terminator, said recessed area extending from a location near said distal end of said catheter terminator to a point intermediate said proximal and distal ends of said catheter terminator, said recessed area being surrounded on circumferentially by a wall portion which is raised with respect to said recessed area, said passageway terminating in an aperture in said recessed area near to the edge of said recessed area, said raised portion of said catheter terminator thereby extending above said recessed area to maintain fibrotic tissue growth away from said recessed area to allow fluid to freely exit said aperture; and a plurality of tapered frictional ridges integrally constructed with said catheter terminator at the proximal end thereof, said tapered frictional ridges allowing said other end of said length of tubing to be slidably installed thereover, and resisting the removal of said other end of said length of tubing from said tapered frictional ridges once installed, said passageway extending centrally through the portion of said catheter terminator containing said tapered frictional ridges.

* * * * *